United States Patent [19]

Saitoh et al.

[11] Patent Number: 4,810,721

[45] Date of Patent: Mar. 7, 1989

[54] PYRROLIDINEAMIDE DERIVATIVE HAVING ANTI-PROLYL ENDOPEPTIDASE

[75] Inventors: Masayuki Saitoh; Takaharu Tanaka; Naoki Higuchi; Masaki Hashimoto, all of Osaka; Harukazu Fukami, Kyoto, all of Japan

[73] Assignee: Suntory Limited, Osaka, Japan

[21] Appl. No.: 121,887

[22] Filed: Nov. 17, 1987

[30] Foreign Application Priority Data

Nov. 18, 1986 [JP]  Japan ................................ 61-274355

[51] Int. Cl.⁴ ..................... C07D 207/00; A61K 31/40
[52] U.S. Cl. ...................................... 514/422; 548/518
[58] Field of Search ......................... 548/518; 514/422

[56] References Cited

U.S. PATENT DOCUMENTS

| | | | |
|---|---|---|---|
| 4,483,991 | 11/1984 | Freed | 548/518 |
| 4,701,465 | 10/1987 | Tanaka et al. | 548/518 |
| 4,757,083 | 7/1988 | Higuchi et al. | 548/518 |

FOREIGN PATENT DOCUMENTS

| | | | |
|---|---|---|---|
| 60-172929 | 9/1985 | Japan | 548/518 |
| 60-188317 | 9/1985 | Japan | 548/518 |
| 61-183297 | 8/1986 | Japan | 548/518 |

OTHER PUBLICATIONS

The Agriculture Chemical Society of Japan, pp. 752–754 (1959).
Journal of Neurochemistry, vol. 41 (1), 69–75 (1983).
Agric. Biol. Chem., 42(12), 2417–2419 (1978).

*Primary Examiner*—Mary C. Lee
*Assistant Examiner*—Robert C. Whittenbaugh
*Attorney, Agent, or Firm*—Cushman, Darby & Cushman

[57] ABSTRACT

A novel pyrrolidineamide derivative that exhibits inhibitory activity toward prolyl endopeptidase and its use as an inhibitor against said enzyme are provided. The pyrrolidineamide of the invention has the following general formula:

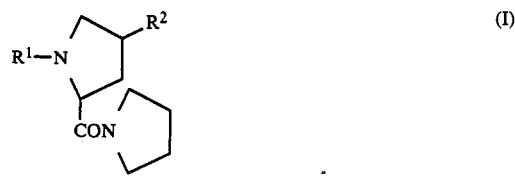

wherein $R^1$ is benzyloxycarbonyl or a group of the formula:

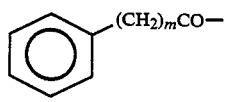

(wherein m is an integer of from 1 to 5) and $R^2$ is hydroxy, acyloxyy or a group of the formula:

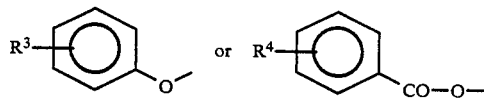

(wherein $R^3$ and $R^4$ independently are a hydrogen atom, a halogen atom, a lower alkyl or a lower alkoxy).

5 Claims, No Drawings

4,810,721

PYRROLIDINEAMIDE DERIVATIVE HAVING ANTI-PROLYL ENDOPEPTIDASE

FIELD OF THE INVENTION

The present invention relates to a novel pyrrolidineamide derivative having the general formula(I):

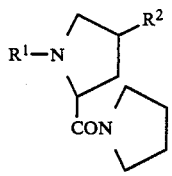
(I)

wherein $R^1$ is benzyloxycarbonyl or a group of the formula:

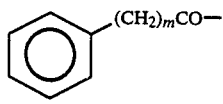

(wherein m is an integer of from 1 to 5) and $R^2$ is hydroxy, acyloxy or a group of the formula:

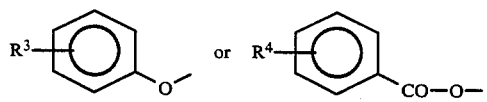

(wherein $R^3$ and $R^4$ independently are a hydrogen atom, a halogen atom, a lower alkyl, preferably an alkyl having 1 to 5 carbon atoms or a lower alkoxy which has preferably 1 to 5 carbon atoms) and the use thereof.

To be more precise, the present invention relates to a novel compound having the general formula (I) that exhibits enzyme inhibitory activity toward prolyl endopeptidase (EC, 3.4.21.26). The invention also relates to such novel compounds and their use as prolyl endopeptidase inhibitors or drugs which contain at least one of said compounds as the active ingredient, especially the use thereof as anti-amnesic agents.

Prolyl endopeptidase is known to inactivate neurotransmitters such as substance P, thyrotropin-releasing hormone (TRH) and neurotensin or vasopressin speculatively associated with memory. Tsuru and Yoshimoto of the Department of Pharmaceutical Science, Nagaskai University, found that compounds capable of inhibiting prolyl endopeptidase activity were effective in preventing experimental amnesia caused in rats by scopolamine, and inferred that prolyl endopeptidase inhibitor would be related to memory fixation (Yoshimoto et al., page 752 of 1984 Proceedings of Annual Meeting, The Agricultural Chemical Society of Japan). Based on this discovery, they suggested the potential use of prolyl endopeptidase inhibitor for prevention and treatment of amnesia. Motivated by this report by Tsuru and Yoshimoto, the present inventors have tried to synthesize compounds which are close to natural substances by combining peptide compounds with amino acids that enjoy a high safety level as natural compounds in order to obtain novel compounds which exhibit strong inhibitory activity toward prolyl endopeptidase while displaying low toxicity.

PRIOR ART

U.S. Ser. No. 760,411 (filed on July 30, 1985), U.S. Ser. No. 852,709 (filed on Apr. 16, 1986), U.S. Ser. No. 852,710 (filed on Apr. 16, 1986) and U.S. Ser. No. 10,490 (filed on Feb. 3, 1987), all of which have been assigned to be assignee of this invention, disclose certain types of compounds which have inhibitory activity and are thus effective for treating amnesia.

SUMMARY OF THE INVENTION

The inventors have now accomplished the present invention based upon their discovery that novel pyrrolidineamide derivative represented by the general formula (I) shown above has anti-prolyl endopeptidase activity.

The compounds of the general formula (I) differ greatly from the conventional anti-amnesic agents of piracetam derivatives in that the former contains hydroxyproline residue or amido derivative thereof. Because they are amino acids and peptide derivative, the compounds of the formula (I) show extremely low toxicity levels in organisms.

DETAILED DESCRIPTION OF THE INVENTION

The compounds having the general formula (I) may be obtained by the methods explained hereunder.

Each of the following abbreviations on the left stand for the words given on the right.

WSCD.HCL: N-ethyl-N',N'-dimethylaminopropyl carbodiimide hydrochloride
DEADC: diethylazide dicarboxylate
TPP: triphenylphosphine
Z: benzyloxycarbonyl The compound of the invention of the general formula (I) wherein $R^2$ is hydroxy, that is, pyrrolidineamide derivative having the general formula (V):

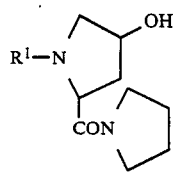
(V)

may be obtained by reacting acylhydroxyproline derivative having the general formula (IV):

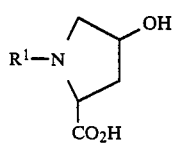
(IV)

wherein $R^1$ has the same meaning as given above, with pyrrolidine in the presence of a condensation agent, such as WSCD.

Pyrrolidineamide derivatives having the general formula (II):

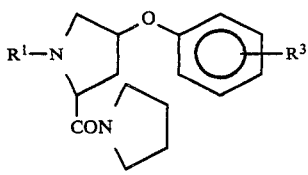

(II)

wherein $R^1$ and $R^3$ have the same meanings given above, may be obtained by reacting the compound of the formula (V) with phenol derivative of the general formula (VI):

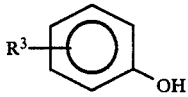

(VI)

wherein $R^3$ has the same meaning as given above, in the presence of dehydration catalyst. As the dehydration catalyst which may be used in this reaction, aromatic sulfonic acid, cation-exchange resin, dicyclohexylcarbodiimide, aluminum chloride, sulfuric acid, hydrochloric acid etc. may be mentioned, and DEACD can be mentioned as the preferred catalyst for use under mild conditions. The solvent may be selected from those which remain inert in the reaction. Especially preferred is tetrahydrofuran.

Pyrrolidineamide derivative of the general formula (III):

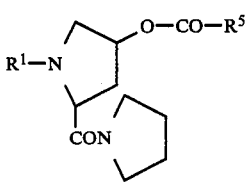

(III)

wherein $R^1$ has the same meaning given above and $R^5$ is a lower alkyl or a group of the formula:

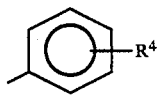

(wherein $R^4$ has the same meaning as given above), may be obtained by reacting the compound of the formula (V) in the presence of base with acid anhydride or carboxylic acid halide having the general formula (VII):

$R^5$—CO—A (VII)

wherein $R^5$ has the same meaning given above, and A is a halogen atom or a group of the formula:

$R^5$—CO—O—

(wherein $R^5$ has the same meaning as given above).

The compound of the formula (III) may also be obtained by reacting the compound (V) in the presence of DEADC and TPP with carboxylic acid having the formula (VIII):

$R^5$—CO.OH (VIII)

wherein $R^5$ has the same meaning as given above.

The compounds of the present invention may exist in cis form as well as trans form, due to the stereochemistry of the hydroxyl group in acylhydroxyproline derivative (IV) used as the starting material. Both those in cis form and those in trans form display anti-prolyl endopeptidase activity and therefore are included within the scope of the present invention.

The present invention is hereunder described in greater detail by way of Examples.

The Preparative Examples exemplify a method for the preparation of starting compounds which may be used in Examples 1 to 4.

PREPARATIVE EXAMPLE (a)

N-Benzyloxycarbonyl-trans-4-hydroxy-L-proline

Trans-4-hydroxy-L-proline (4.7 g) was dissolved in 2N sodium hydroxide (36 ml), to which benzyloxycarbonylchloride (6.1 g) was slowly added dropwise under cooling with ice water. The mixture was then stirred at room temperature throughout a whole day and night. After the reaction, the mixture was washed with ethyl acetate, and to the aqueous layer was then added sodium chloride to saturation. Then the pH was adjusted to around 3 with 10N hydrochloric acid and the mixture was extracted with ethyl acetate. The organic layer was washed with saturated solution of sodium chloride in water and it was then dried over anhydrous magnesium sulfate. The solvent was removed under reduced pressure whereby the titled compound (6.9 g) was obtained.

PREPARATIVE EXAMPLE (b)

N-(4-phenylbutanoyl)-trans-4-hydroxy-L-proline was obtained by repeating the process of Preparative Example (a) but using 4-phenylbutanoyl chloride in place of benzyloxycarbonyl chloride.

PREPARATIVE EXAMPLE (c)

N-(4-phenylbutanoyl)-cis-4-hydroxy-L-proline was obtained by repeating the same process as in Preparative Example (a) but employing 4-phenylbutanoyl chloride in place of benzyloxycarbonyl chloride, and cis-4-hydroxy-L-proline in place of trans-4-hydroxy-L-proline.

EXAMPLE 1

N-[N-(4-phenylbutanoyl)-trans-4-hydroxy-L-prolyl]-pyrrolidine (a) N-(4-phenylbutanoyl)-trans-4-hydroxy-L-proline (570 mg), pyrrolidine (140 mg) and WSCD.HCl (380 mg) were dissolved in dry methylene chloride (20 ml) and stirred at room temperature throughout a whole day and night. The reaction mixture was concentrated under reduced pressure. The resulting residue was purified by medium pressure column chromatography on silica gel (solvent: chloroform-methanol) whereby N-[N-(4-phenylbutanoyl)-trans-4-hydroxy-L-prolyl]pyrrolidine (520 mg) (SUAM 14432) was obtained.

(b) By employing N-(4-phenylbutanoyl)-cis-4-hydroxy-L-proline in place of N-(4-phenylbutanoyl)-trans-4-hydroxy-L-proline in the procedure of Example 1(a) given above, N-[N-(4-phenylbutanoyl)-cis-4-hydroxy-L-prolyl]pyrrolidine (SUAM 14496) was obtained.

EXAMPLE 2

N-[N-(4-phenylbutanoyl)-cis-4-phenoxy-L-prolyl]pyrrolidine (a) N-[N-(4-phenylbutanoyl)-trans-4-hydroxy-L-prolyl]pyrrolidine (800 mg), TPP (640 mg), DEADC (420 mg) and phenol (230 mg) were dissolved in dry tetrahydrofuran (50 ml) and stirred under nitrogen atmosphere at room temperature throughout a whole day and night. The solvent was removed under reduced pressure and the resulting residue was purified by medium pressure column chromatography on silica gel (Solvent: ethyl acetate-methanol) whereby N-[N-(4-phenylbutanoyl)-cis-4-phenoxy-L-prolyl]pyrrolidine (300 mg) (SUAM 14504) was obtained.

By employing (i) 4-chlorophenol, (ii) 4-methylphenol, (iii) 2-methoxyphenol, (iv) 3-methoxyphenol and (v) 4-methoxyphenol in place of phenol in the procedure of Example 2(a) above:
(i) N-[N-(4-phenylbutanoyl)-cis-4-(4-chlorophenoxy)-L-prolyl]pyrrolidine (SUAM 14508);
(ii) N-[N-(4-phenylbutanoyl)-cis-4-(4-methylphenoxy)-L-prolyl]pyrrolidine (SUAM 14509);
(iii) N-[N-(4-phenylbutanoyl)-cis-4-(2-methoxyphenoxy)-L-prolyl]pyrrolidine (SUAM 14467);
(iv) N-[N-(4-phenylbutanoyl)-cis-4-(3-methoxyphenoxy)-L-prolyl]pyrrolidine (SUAM 14468); and
(v) N-[N-(4-phenylbutanoyl)-cis-4-(4-methoxyphenoxy)-L-prolyl]pyrrolidine (SUAM 14441)
were respectively obtained.

(b) By repeating the process of Example 2(a) above but using N-(N-benzyloxycarbonyl-trans-4-hydroxy-L-prolyl)pyrrolidine in place of N-[N-(4-phenylbutanoyl)-trans-4-hydroxy-L-prolyl]pyrrolidine and 4-methoxyphenol in place of phenol, N-[N-benzyloxycarbonyl-cis-4-(4-methoxyphenoxy)-L-prolyl]pyrrolidine (SUAM 14491) was obtained.

EXAMPLE 3

N-[N-(4-phenylbutanoyl)-trans-4-(4-chlorobenzoyloxy)-L-prolyl]pyrrolidine (a) N-[N-(4-phenylbutanoyl)-trans-4-hydroxy-L-prolyl]pyrrolidine (660 mg) and triethylamine (0.3 ml) were dissolved in methylene chloride (20 ml), to which 4-chlorobenzoyl chloride (390 mg) was added dropwise under cooling with ice. The mixture was stirred at room temperature throughout a whole day and night. Then the solvent was removed under reduced pressure and the resulting residue was purified by medium pressure column chromatography on silica gel whereby N-[N-(4-phenylbutanoyl)-trans-4-(4-chlorobenzoyloxy)-L-prolyl]pyrrolidine (480 mg) (SUAM 14499) was obtained.

By employing (i) benzoyl chloride, or (ii) 4-methoxybenzoyl chloride in place of 4-chlorobenzoyl chloride in the procedure of Example 3(a) given above, the products:
(i) N-[N-4-phenylbutanoyl)-trans-4-benzoyloxy-L-prolyl]pyrrolidine (SUAM 14498); and
(ii) N-[N-4-phenylbutanoyl)-trans-4-(4-methoxybenzoyloxy-L-prolyl]pyrrolidine (SUAM 14497)
were respectively obtained.

(b) By employing N-[N-(4-phenylbutanoyl)-cis-4-hydroxy-L-prolyl]pyrrolidine in place of N-[N-(4-phenylbutanoyl)-trans-4-hydroxy-L-prolyl]pyrrolidine in the procedure of Example 3(a) above, N-[N-(4-phenylbutanoyl)-cis-4-(4-chlorobenzoyloxy)-L-prolyl]pyrrolidine (SUAM 14503) was obtained.

By using (i) benzoyl chloride, or (ii) 4-methoxybenzoyl chloride in place of 4-chlorobenzoyl chloride in the above procedure, the products:
(i) N-[N-(4-phenylbutanoyl)-cis-4-benzoyloxy-L-prolyl]pyrrolidine (SUAM 14502); and
(ii) N-[N-(4-phenylbutanoyl)-cis-4-(4-methoxybenzoyloxy-L-prolyl]pyrrolidine (SUAM 14501)
were respectively obtained.

EXAMPLE 4

N-[N-(4-phenylbutanoyl)-trans-4-acetoxy-L-prolyl]pyrrolidine (a) N-[N-(4-phenylbutanol)-trans-4-hydroxy-L-prolyl]pyrrolidine (30 mg) was dissolved in acetic anhydride (0.25 ml) and pyridine (0.25 ml) and then the mixture was maintained at room temperature for a whole day and night. The mixture was poured into ice water and then extracted with ethyl acetate. The organic layer was washed successively with diluted hydrochloric acid, saturated sodium bicarbonate solution and water in that order, and was then dried over anhydrous sodium sulfate. The solvent was removed under reduced pressure whereby N-[N-(4-phenylbutanoyl)-trans-4-acetoxy-L-prolyl]pyrrolidine (30 mg) (SUAM 14506) was obtained.

(b) By employing N-[N-(4-phenylbutanoyl)-cis-4-hydroxy-L-prolyl]pyrrolidine in place of N-[N-(4-phenylbutanoyl)-trans-4-hydroxy-L-prolyl]pyrrolidine in the procedure of Example 4(a) above, N-[N-(4-phenylbutanoyl)-cis-4-acetoxy-L-prolyl]pyrrolidine (SUAM 14507) was obtained.

All the compounds obtained are novel and the physicochemical data on them are shown in Table 1.

All the compounds listed in Table 1 are soluble in chloroform, methylene chloride, ethyl acetate and methanol.

The results of examination of the compound of the invention with respect to its action for inhibiting digestion of Z-glycyl-prolyl-$\beta$-naphthylamide by prolyl endopeptidase indicate that the compound of the invention exhibits a strong anti-prolyl endopeptidase activity while showing no inhibition against proteinases, such as papain, bromelain, trypsin, chymotrypsin, thermolysin, pepsin etc., as shown in Example 5 given below.

TABLE 1

| Example No. | SUAM No. | Nature | IR spectrum (Film, cm$^{-1}$) | NMR spectrum (CDCl$_3$, TMS standard $\delta$) |
|---|---|---|---|---|
| 1 | 14432 | oil | 3400 (br), 1630, 1450, 1450, 750, 700 | 1.82–2.26(10H,m), 2.53–2.75(2H,m), 3.30–3.80(6H,m), 4.17(1H,d,J = 3.6 Hz), 4.66(1H,t,J = 7.8 Hz), 4.60(1H,m), 7.16(5H,s) |
| 1 | 14496 | oil | 3300 (br), 1620, 1430, 750, 700 | 1.72–2.38(10H,m), 2.68(2H,m), 3.42–3.64(5H,m), 4.10(1H,m), 4.40(1H,m), 4.72(1H,d,J = 2.0, 9.0 Hz), 6.37(1H,d,J = 12 Hz), 7.21(5H,s) |

TABLE 1-continued

| Example No. | SUAM No. | Nature | IR spectrum (Film, cm$^{-1}$) | NMR spectrum (CDCl$_3$, TMS standard δ) |
|---|---|---|---|---|
| 2 | 14504 | oil | 2950, 2870, 1640, 1430, 1240, 750, 700 | 1.74–2.82(12H,m), 3.06–4.00(6H,m), 4.62(1H,dd,J = 6.6, 8.4 Hz), 4.81(1H,m), 6.24–7.36(5H,m), 7.15(5H,s) |
| 2 | 14508 | oil | 2950, 2870, 1640, 1440, 1240, 830, 750, 700 | 1.80–2.82(12H,m), 3.12–4.02(6H,m), 4.50–4.90(2H,m), 7.14(5H,s), 6.72(2H,d,J = 9.6 Hz), 7.10–7.34(2H) |
| 2 | 14509 | oil | 2950, 2870, 1640, 1430, 1230, 820, 750, 710 | 1.83–2.77(12H,m), 2.27(3H,s), 3.10–4.14(6H,m), 4.40–4.90(2H,m) 6.68, 7.03(2H each, both d, J = 9.6 Hz), 7.16(5H,s) |
| 2 | 14467 | oil | 2950, 2880, 1640, 1440, 1250, 750, 700 | 1.83–2.78(12H,m), 3.14–3.85(6H,m), 3.80(3H,s), 4.47–4.95(2H,m), 6.88(4H,s), 7.16(5H,s) |
| 2 | 14468 | oil | 2950, 2870, 1640, 1440, 1150, 750, 700 | 1.78–2.75(12H,m), 3.10–3.85(6H,m), 3.70(3H,s), 4.62(1H,dd,J = 7.2, 8.4 Hz), 4.80(1H,m), 6.37(3H,m), 7.14(6H,s) |
| 2 | 14441 | oil | 2950, 2870, 1640, 1430, 1220, 1030, 820, 740, 700 | 1.78–2.74(12H,m), 3.24–3.96(6H,m), 3.78(3H,s), 4.66(1H,dd,J = 7.0, 8.0 Hz), 4.78(1H,quintet,J = 7.0 Hz), 6.84(4H,s), 7.20(5H,s) |
| 2 | 14491 | oil | 2950, 2880, 1700, 1650, 1420, 1230, 830, 750, 700 | 1.80–2.76(6H,m), 3.14–3.70(6H,m), 3.78(3H,s), 4.50(1H,m), 4.78(1H,m), 5.10(2H,m), 6.82(4H,s), 7.32(5H,s) |
| 3 | 14499 | oil | 2970, 2950, 2870, 1720, 1640, 1430, 1270, 850, 760, 700 | 1.73–2.75(12H,m), 3.22–4.18(6H,m), 4.81(1H,t,J = 7.8 Hz), 5.62(1H,m), 7.12(5H,s), 7.32, 7.86(2H each, both d, J = 8.4 Hz) |
| 3 | 14498 | oil | 2970, 2950, 2870, 1720, 1640, 1440, 1270, 740, 710 | 1.82–2.77(12H,m), 3.22–4.12(6H,m), 4.80(1H,t,J = 7.2 Hz), 5.60(1H,m), 7.12(5H,s), 7.30–8.02(5H,m) |
| 3 | 14497 | oil | 2970, 2950, 2870, 1710, 1640, 1440, 1260, 850, 750, 700 | 1.81–2.77(12H,m), 3.23–4.16(6H,m), 3.81(3H,s), 4.81(1H,t,J = 7.8 Hz), 5.55(1H,m), 6.85, 7.89(2H each, both d, J = 8.4 Hz), 7.14(5H,s) |
| 3 | 14503 | oil | 2970, 2950, 2870, 1710, 1640, 1420, 1270, 850, 760, 750, 700 | 1.70–2.78(12H,m), 3.18–4.08(6H,m), 4.70(1H,dd,J = 5.4, 8.4 Hz), 5.42(1H,m), 7.14(5H,s), 7.33, 7.91(2H each, both d, J = 9.0 Hz) |
| 3 | 14502 | oil | 2970, 2950, 2880, 1720, 1640, 1430, 1270, 750, 710 | 1.80–2.77(12H,m), 3.20–4.10(6H,m), 4.70(1H,dd,J = 6.0, 9.0 Hz), 5.42(1H,m), 7.15(5H,s), 7.34–8.07(5H,m) |
| 3 | 14501 | oil | 2950, 1700, 1640, 1420, 1250, 850, 750, 700 | 1.82–2.86(12H,m), 3.20–4.10(6H,m), 3.79(3H,s), 4.69(1H,dd,J = 5.4, 9.0 Hz), 5.40(1H,m), 6.85, 7.93(2H each, both d, J = 8.4 Hz) |
| 4 | 14506 | oil | 2950, 2870, 1740, 1640, 1430, 1240, 740, 700 | 1.87–2.40(10H,m), 2.05(3H,s), 2.56–2.80(2H,m), 3.34–4.08(6H,m), 4.73(1H,t,J = 8.0 Hz), 5.34(1H,m), 7.17(5H,s) |
| 4 | 14507 | oil | 2950, 2870, 1730, 1640, 1430, 1240, 750, 700 | 1.88–2.42(10H,m), 2.05(3H,s), 2.66(2H,m), 3.26–4.02(6H,m), 4.63(1H,dd,J = 6.0, 9.0 Hz), 5.14(1H,quintet,J = 7.0 Hz), 7.20(5H,s) |

EXAMPLE 5

Measurement of Anti-Prolyl Endopeptidase Activity

The method of Yoshimoto and Tsuru [T. Yoshimoto and D. Tsuru, Agric. Biol. Chem., 42, 2417 (1978)] was used to measure the anti-prolyl endopeptidase activities of several compounds of the present invention. A mixture of 0.0025M Z-glycyl-prolyl-β-naphthylamide (0.25 ml), 0.1M phosphate buffer (pH, 7.0; 0.99 ml) and a solution of a particular anti-prolyl endopeptidase compound (0.01 ml) was incubated in a test tube at 37° C. for 3 minutes. Thereafter, 0.1 ml of a solution of prolyl endopeptidase (0.2 U/ml) was added and the mixture was incubated at 35° C. for 10 minutes. After the reaction, 2.0 ml of Triton X-100 in 1M acetate buffer (pH, 4.0) was added to the reaction mixture so that the final concentration of the surfactant might be 10%. The mixture was left at room temperature for 15 minutes and the absorbance (a) at 410 nm was measured.

A sample of a blind test was prepared by using the buffer instead of the anti-prolyl endopeptidase compound and its absorbance (b) was also measured. The percentage of inhibition against prolyl endopeptidase was calculated by the formula:

$$[(b-a)/b] \times 100$$

and the amount of a specific compound need to achieve 50% inhibition (IC$_{50}$) was determined. The results are shown in Table 2.

TABLE 2

| Compound No. | IC$_{50}$ (μg/test tube) |
|---|---|
| SUAM 14432 | 0.07 |
| SUAM 14496 | 0.10 |
| SUAM 14504 | 0.02 |
| SUAM 14508 | 0.04 |
| SUAM 14509 | 0.03 |
| SUAM 14467 | 0.008 |
| SUAM 14468 | 0.03 |

TABLE 2-continued

| Compound No. | IC$_{50}$ (μg/test tube) |
| --- | --- |
| SUAM 14441 | 0.01 |
| SUAM 14491 | 0.04 |
| SUAM 14499 | 0.20 |
| SUAM 14498 | 0.30 |
| SUAM 14497 | 0.15 |
| SUAM 14503 | 0.06 |
| SUAM 14502 | 0.06 |
| SUAM 14501 | 0.04 |
| SUAM 14506 | 0.03 |
| SUAM 14507 | 0.10 |

The compounds of the invention exhibit strong inhibitory activity toward prolyl endopeptidase and yet display extremely low toxicity levels in organisms. They are therefore useful for the preparation and treatment of amnesia.

EXAMPLE 6

Measurement of the Memory-Fixation Effect of the Inventive Compound

The measurement was conducted in accordance with the method described in Experientia 40, 506 (1984) with a slight modification made by the inventors. Several of the compounds of the invention were checked for their ability to enhance long-term memory fixation in the passive avoidance learning method using an apparatus which has an electrifiable grid floor and a refuge platform on one end of the floor. Solutions of physiological saline which contained 1 mg/kg–3 mg/kg of selected compound of the present invention were administered per os to DDY strain male mice weighing 37–43 g. One hour after the administration, electric shocks were applied to the mice in a black box so that they would acquire passive avoidance learning.

The results of the test were assessed 24 hours after the learning in terms of the memory fixation acquired in the passive avoidance learning by measuring the residence time (latency) during which the mice stayed on the platform. The results between the test groups which received the test compound and the control group which received physiological saline in place of the test compound were compared.

The results are give the Table 3.

TABLE 3

| Memory fixation test in mice | | | |
| --- | --- | --- | --- |
| Sample | Dose (mg/kg) | Number of mice | Latency (sec.) |
| physiological saline | | 10 | 47 |
| SUAM-14441 | 1.0 | 5 | 101 |
| SUAM-14432 | 3.0 | 5 | 153 |
| SUAM-14432 | 1.0 | 5 | 76 |
| SUAM-14496 | 3.0 | 5 | 135 |
| SUAM-14496 | 1.0 | 5 | 138 |
| SUAM-14496 | 0.3 | 5 | 147 |
| SUAM-14401 | 3.0 | 5 | 143 |
| SUAM-14509 | 3.0 | 5 | 95 |
| SUAM-14506 | 3.0 | 5 | 64 |
| SUAM-14507 | 3.0 | 5 | 53 |

The formulation of the agent of the invention includes either solid formulations such as capsules, tablets and powders, or liquid formations such as exlixirs, syrups and suspensions for oral administration. Alternatively, the active compounds (I) may be formulated as injections or suppositories.

The carrier included in the agent of the invention may be selected from pulverulent solid carriers such as lactose, saccharose, dextrose, mannitol, sorbitol, cellulose and glycine etc.

The agent of the invention may further contain a lubricant, a binder or a disintegrator. Examples of suitable lubricants are silicon dioxide, talc, magnesium stearate and polyethylene glycol. Examples of suitable binders are starch, gelatin, tragacanth, methyl cellulose, sodium carboxymethyl cellulose and polyvinyl pyrrolidone. Examples of suitable disintegrators are starch and agar etc.

The compound of the invention is orally administered to an adult patient in a dose of 10 to 4000 mg/day, preferably 100 to 1000 mg/day, or administered parenterally in a dose of 1 to 2000 mg/day, preferably 50 to 500 mg/day. The dose may be varied according to the disease, age, weight or condition of the patient or the formulation of the drugs.

FORMULATION 1

| Ingredient | part |
| --- | --- |
| Compound of the formula (I) (SUAM 14467) | 45 |
| Starch | 15 |
| Lactose | 40 |

The ingredients are mixed thoroughly, and tablets or capsules are formulated from the mixture.

| Ingredient | part |
| --- | --- |
| Compound of the formula (I) (SUAM 14467) | 1 |
| Surface active agent | 5 |
| Physiological saline | 94 |

The above ingredients are mixed under warming, and dispensed under sterile conditions into ampoules for use as injections.

What is claimed is:

1. A pyrrolidineamide derivative of the formula (I):

$$R^1-N\begin{array}{c}\diagup\diagdown^{R^2}\\ \diagdown\diagup\\ CON\end{array}$$ (I)

wherein $R^1$ is benzoyloxycarbonyl or a group of the formula:

$$\text{(phenyl)}(CH_2)_mCO-$$

(wherein m is an integer of from 1 to 5) and $R^2$ is hydroxy, lower alkanoyloxy or a group of the formula:

$$R^3-\text{(phenyl)}-O- \quad \text{or} \quad R^4-\text{(phenyl)}-CO-O-$$

(wherein $R^3$ and $R^4$ independently are a hydrogen atom, a halogen atom, a lower alkyl or a lower alkoxy).

2. A compound according to claim 1 having the formula (II):

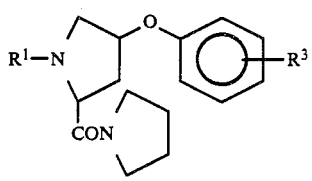

wherein $R^1$ is as defined in claim 1 and $R^3$ is a hydrogen atom, a halogen atom, a lower alkyl or a lower alkoxy.

3. A compound according to claim 1 having the formula (III):

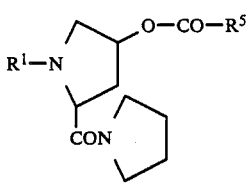

wherein $R^1$ is as defined in claim 1 and $R^5$ is lower alkyl or a group of the formula:

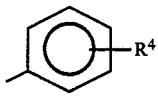

(wherein $R^4$ is a hydrogen atom, a halogen atom, a lower alkyl or a lower alkoxy).

4. A pharmaceutical composition containing as the active ingredient a pharmaceutically effective amount of a novel pyrrolidineamide derivative having the formula (I):

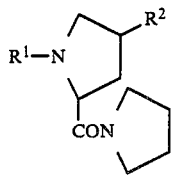

wherein $R^1$ is benzyloxycarbonyl or a group of formula:

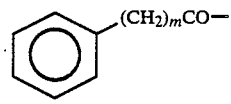

(wherein m is an integer of from 1 to 5) and $R^2$ is hydroxy, lower alkanoyloxy or a group of the formula:

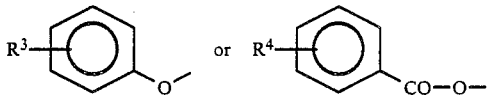

(wherein $R^3$ and $R^4$ independently are a hydrogen atom, a halogen atom, a lower alkyl or a lower alkoxy), together with a pharmaceutically acceptable diluent or carrier.

5. A composition according to claim 4 which is used for alleviating amnesia.

* * * * *